(12) United States Patent
Schmidt

(10) Patent No.: US 8,710,292 B2
(45) Date of Patent: Apr. 29, 2014

(54) DEHYDRATABLE HYGIENE ARTICLES

(76) Inventor: Harald Schmidt, Muelheim/Ruhr (DE)

( * ) Notice: Subject to any disclaimer, the term of this patent is extended or adjusted under 35 U.S.C. 154(b) by 537 days.

(21) Appl. No.: 12/376,037

(22) PCT Filed: Jul. 31, 2007

(86) PCT No.: PCT/EP2007/006760
§ 371 (c)(1),
(2), (4) Date: Mar. 5, 2009

(87) PCT Pub. No.: WO2008/014972
PCT Pub. Date: Feb. 7, 2008

(65) Prior Publication Data
US 2009/0326497 A1    Dec. 31, 2009

(30) Foreign Application Priority Data
Jul. 31, 2006   (DE) .......................... 10 2006 035 945

(51) Int. Cl.
*A61F 13/15*     (2006.01)
*A61F 13/20*     (2006.01)

(52) U.S. Cl.
USPC ...................... 604/367; 604/385.01; 604/378

(58) Field of Classification Search
USPC .............................. 604/367, 375, 378, 385.01
See application file for complete search history.

(56) References Cited

U.S. PATENT DOCUMENTS

| | | | |
|---|---|---|---|
| 5,124,126 A | 6/1992 | Ripp | |
| 6,696,618 B2 | 2/2004 | Dodge, II et al. | |
| 7,175,613 B2 * | 2/2007 | Sugiyama et al. | ....... 604/385.14 |
| 2003/0199844 A1 | 10/2003 | La Von et al. | |

FOREIGN PATENT DOCUMENTS

| | | |
|---|---|---|
| DE | 29607480 U1 | 7/1996 |
| JP | 2003300051 A | 10/2003 |

* cited by examiner

*Primary Examiner* — Michele M Kidwell
(74) *Attorney, Agent, or Firm* — Laurence A. Greenberg; Werner H. Stemer; Ralph E. Locher

(57) ABSTRACT

A dehydratable hygiene article contains a lower layer which is impermeable to aqueous liquids, an upper layer which is permeable to aqueous liquids, a core disposed between the lower and upper layer and absorbs aqueous liquids, and a trigger system containing a superabsorbent material which is capable of absorbing aqueous liquids with the formation of a hydrogel. After the trigger system has been activated, at least some of the aqueous liquid absorbed can be released from the superabsorbent material when it is present as a hydrogel. The hygiene article contains at most 50 wt. % of a further superabsorbent material. Based on the total weight of superabsorbent material and further superabsorbent material, which would be capable, after the trigger system has been activated, of at least partly absorbing, with the formation of hydrogel, the aqueous liquid which is at least partly released.

8 Claims, 4 Drawing Sheets

DEHYDRATABLE HYGIENE ARTICLES

BACKGROUND OF THE INVENTION

1. Field of the Invention

The invention relates to dehydratable hygiene articles, a method for dehydrating a hygiene article, a device for dehydrating a dehydratable hygiene article comprising a water-absorbing material, the use of a device for dehydrating hygiene articles and kits.

Hygiene articles, such as, for example, nappies or sanitary towels, contain so-called superabsorbers as liquid-absorbing materials. These superabsorbers are water-insoluble, crosslinked polymers which are capable of absorbing, with swelling and formation of hydrogels, and retaining under a certain pressure large amounts of aqueous liquids, in particular body fluids, preferably urine or blood.

As a rule, these hygiene articles are disposable products. By the absorption of body fluids by the superabsorbers, however, these hygiene articles swell greatly, so that a significant increase in the volume of the hygiene article occurs. This increase in the volume of the hygiene article is a disadvantage, however, since especially in households with several wearers of hygiene articles, for example in families with several infants wearing nappies, the proportion by volume of the nappies in the total leftover refuse produced is very high.

Various approaches as to how the problems associated with the large volume of refuse caused by used hygiene articles can be solved are described in the literature.

Thus, GB-A-2284820 describes flushable products which have a wet strength sufficient for their use as intended, in particular during long-lasting or extended use in the presence of body fluids and at temperatures of above 25° C., but which disintegrate and become finely divided in the present of ordinary tap water. The disadvantage of the method described in this prior art for reducing the volume of refuse caused by swollen hygiene articles is, however, that the individual components of the hygiene article cannot be fed to refuse disposal and therefore recycled, but instead are dissolved in the tap water and are disposed of in this dissolved state via the sewerage system. This method and manner of refuse removal is unacceptable, however, since the individual components of the hygiene articles can adversely influence the quality of the ground water.

DE 296 07 480 U1 discloses a nappy refuse press having a hollow cavity, at least two flat elements which are constructed movably with respect to one another, wherein the two flat elements are joined to one another with a joining element and are arranged one above the other to form the hollow cavity, and wherein an opening is constructed in one flat element. A refuse bag filled with disposable nappies is deposited through this opening. By pressing together the two flat elements, a large proportion of the air contained in the nappy refuse is driven out. The disadvantage of the method described in this prior art is that a really efficient reduction in the volume of refuse cannot be achieved.

2. Brief Summary of the Invention

The present invention was based on the object of overcoming the disadvantages resulting from the prior art.

In particular, the present invention was based on the object of providing hygiene articles which, after they have been used, lead to a lower volume of refuse compared with conventional hygiene articles.

The present invention was also based on the object of providing hygiene articles which can be disposed of with a relatively small volume of refuse simply and in an environmentally friendly manner via leftover refuse. In this context, the disposable of the hygiene articles as far as possible should not lead to pollution of the ground water.

The present invention was furthermore based on the object of providing a device by means of which the volume of used hygiene articles can be reduced as efficiently as possible compared with the devices known from the prior art.

A contribution towards achieving the abovementioned objects is made by a dehydratable hygiene article comprising:
i) a lower layer which is impermeable to aqueous liquids,
ii) an upper layer which is permeable to aqueous liquids,
iii) a core which is arranged between the lower and the upper layer and absorbs aqueous liquids, and
iv) a trigger system comprising a superabsorbent material (a) which is capable of absorbing aqueous liquids with the formation of a hydrogel, wherein after the trigger system has been activated, at least some of the aqueous liquid absorbed can be released from the superabsorbent material (a) when this is present as a hydrogel,
wherein the hygiene article comprises at most 50 wt. %, preferably at most 25 wt. %, more preferably at most 10 wt. %, still more preferably at most 5 wt. %, even still more preferably at most 1 wt. % of a further superabsorbent material (b), in each case based on the total weight of superabsorbent material (a) and superabsorbent material (b), but most preferably no further superabsorbent material (b) which would be capable, after the trigger system (iv) has been activated, of at least partly absorbing, with the formation of a hydrogel, the aqueous liquid which is at least partly released, optionally only after a further trigger system which differs from the trigger system (iv) has been activated.

According to a particular embodiment of this hygiene article according to the invention, this is characterized by a compressibility factor, determined in accordance with the test method described herein, of at least 1.1, preferably at least 1.5, particularly preferably at least 2, more preferably at least 3, still more preferably at least 4 and most preferably at least 5.

A contribution towards achieving the abovementioned objects is also made by a dehydratable hygiene article comprising:
i) a lower layer which is impermeable to aqueous liquids,
ii) an upper layer which is permeable to aqueous liquids,
iii) a core which is arranged between the lower and the upper layer and absorbs aqueous liquids, and
iv) a trigger system comprising a superabsorbent material (a) which is capable of absorbing aqueous liquid with the formation of a hydrogel, wherein after the trigger system has been activated, at least some of the aqueous liquid absorbed can be released from the superabsorbent material (a) when this is present as a hydrogel,
wherein the hygiene article has a compressibility factor, determined in accordance with the test method described herein, of at least 1.1, preferably at least 1.5, still more preferably at least 2, more preferably at least 3, still more preferably at least 4 and most preferably at least 5.

Preferred hygiene articles are nappies, sanitary towels, inserts for briefs, bed undersheets or incontinence pads, nappies and sanitary towels being particularly preferred and nappies being the most preferred hygiene articles. In this context, the term "nappy" relates quite generally to an absorbent piece of clothing which is worn either by infants to absorb liquid or by people with incontinence problems.

The term "superabsorbent" for a particular material indicates that in contact with 0.9 wt. % strength aqueous NaCl solution, this material is capable of retaining at least 25 times, preferably at least 30 times, still more preferably at least 40 times and most preferably 50 to 60 times its own weight of this aqueous NaCl solution in accordance with the test method of ERT 441.2-02.

Hygiene articles with components i) to iv) are known in principle from U.S. Pat. No. 6,696,618. However, the hygiene articles described in U.S. Pat. No. 6,696,618 always contain, in addition to the dehydratable, superabsorbent material, always further superabsorbent material which is capable of absorbing the liquids released during the dehydration, so that overall a hygiene article which shows leakage properties which are as advantageous as possible is present. Dehydration of the hygiene articles which would be associated with a reduction in volume, however, is not possible with the hygiene articles described in U.S. Pat. No. 6,696,618.

Preferred embodiments of a hygiene article according to the invention are explained in more detail in the following by the example of a nappy according to the invention. With respect to the nature of the materials employed, however, these statements also apply to other hygiene articles, such as, for example, sanitary towels.

Materials which are preferably employed for the lower layer (i) which is impermeable to aqueous liquids are those such as are described as the "outer layer which is impermeable to liquid" in DE 695 21 888 T2. The disclosure of DE 695 21 888 T2 with respect to the individual components of a hygiene article, in particular a nappy, is introduced herewith as reference and forms part of the disclosure of the present invention. Preferably, the impermeable lower layer (i) is made of a flexible woven or nonwoven material. According to a particularly preferred embodiment of the dehydratable nappy according to the invention, the impermeable lower layer (i) is a polyethylene film having a thickness in a range of from 0.005 to 0.1 mm, particularly preferably in a range of from 0.01 to 0.05 mm. The impermeable lower layer (i) can furthermore be embossed or provided with a felt in order to impart to the nappy the impression of a piece of clothing. According to a particular embodiment of the dehydratable nappy according to the invention, the impermeable lower layer (i) is a breathable material which is indeed impermeable to aqueous liquids, but not to water vapour. In this connection, it is preferable for the hygiene article to have as a further component a hydrophobic barrier substance located between the impermeable lower layer (i) and the absorbent core (iii), as is described in DE 697 19 217 T2, which is likewise introduced herewith as reference and the disclosure of which with respect to the structural construction of a hygiene article forms part of the disclosure of the present invention. Preferred layers which are permeable to water vapour but impermeable to water in liquid form and preferred hydrophobic barrier substances are those materials which are mentioned in DE 697 19 217 T2 as materials which are preferred for the "breathable outer covering which is impermeable to liquid" or, respectively, for the "hydrophobic barrier substance".

The upper layer (ii) which are permeable to aqueous liquids preferably means layers which are described in DE 695 21 888 T2 as the "top layer". Preferably, the upper layer (ii) which is permeable to aqueous liquids means woven or nonwoven materials and polymer materials, such as thermoplastic films constructed with openings, porous foams, meshed foams, meshed thermoplastic films or the like. The woven or nonwoven materials can be made of natural fibres, such as, for example, cellulose fibres or cotton fibres, of synthetic fibres, such as, for example, polyether fibres, polypropylene fibres or polyethylene fibres, or a mixture of natural or synthetic fibres.

Absorbent cores which are preferably used as the core (iii) which is arranged between the lower and the upper layer (i) and, respectively, (ii) and absorbs aqueous liquids are those which comprise a superabsorbent material and a preferably non-superabsorbent fibre material as the substrate, the superabsorbent material in the absorbent core preferably being the superabsorbent material (a) which is a constituent of the trigger system (iv). In this context, "non-superabsorbent" is preferably understood as meaning a material which is capable of retaining less than 10 g/g, particularly preferably less than 5 g/g of 0.9 wt. % strength NaCl solution in accordance with the test method of ERT 441.2-02.

Superabsorbent materials which are preferred according to the invention are, preferably, synthetic polymer fibres, polymer foams or polymer particles, fibres and particles being preferred and particles being particularly preferred.

Superabsorbent polymer fibres which are preferred according to the invention thus have dimensions such that they can be incorporated into or as yarns for textiles and also directly into textiles. It is preferable according to the invention for the superabsorbent polymer fibres to have a length in the range of from 1 to 500 mm, preferably 2 to 500 mm and particularly preferably 5 to 100 mm and a diameter in the range of from 1 to 200 denier, preferably 3 to 100 denier and particularly preferably 5 to 60 denier.

Superabsorbent polymer particles which are particularly preferred according to the invention have dimensions such that they have an average particle size in accordance with ERT 420.2-02 (ERT=EDANA recommended test method) in the range of from 10 to 3,000 µm, preferably 20 to 2,000 µm and particularly preferably 150 to 850 µm. It is furthermore preferable according to the invention for the superabsorbent polymer particles to be based to the extent of at least 25 wt. %, preferably to the extent of at least 50 wt. % and most preferably to the extent of at least 75 wt. % on particles having a particle size in a range of from 300 to 600 µm.

It is furthermore preferable for the superabsorbent material to have in the absorbent core (iii) at least one of the, preferably all the following properties:

(A) maximum absorption of 0.9 wt. % strength NaCl solution in accordance with ERT 440.2-02 in a range of from at least 10 to 1,000 g/g, preferably from 15 to 500 g/g and particularly preferably from 40 to 150 g/g (in the case of particles, determined for the total particle fraction), (B) the content which can be extracted with 0.9 wt. % strength aqueous NaCl in accordance with ERT 470.2-02 is less than 30 wt. %, preferably less than 20 wt. % and particularly preferably less than 15 wt. %, (C) the bulk density in accordance with ERT 460.2-02 is in the range of from 300 to 1,000 g/l, preferably 310 to 800 g/l and particularly preferably 320 to 750 g/l, (D) the retention capacity in accordance with ERT 441.2-02 is in the range of from 10 to 100 g/g, preferably 15 to 80 g/g and particularly preferably 20 to 60 g/g (in the case of particles, determined for the total particle fraction), (E) the AAP value in accordance with ERT 442.2-02 under a pressure of 0.3 psi is in the range of from 10 to 60 g/g, preferably 15 to 50 g/g and particularly preferably 20 to 45 g/g (in the case of particles, determined for the total particle fraction).

Fibre materials which can be contained as a substrate in the absorbent core (iii) include naturally occurring fibres (modified or non-modified) and also synthetic fibres. Examples of suitable non-modified and modified naturally occurring fibres include cotton, esparto grass, sugar cane, kemp, flax, silk, wool, cellulose, chemically modified cellulose, jute, rayon, ethylcellulose and cellulose acetate. Suitable synthetic fibres can be prepared from polyvinyl chloride, polyvinyl fluoride, polytetrafluoroethylene, polyvinylidene chloride, polyacrylate, such as Orlon®, polyvinyl acetate, polyethylvinyl acetate, insoluble or soluble polyvinyl alcohol, polyolefins, such as polyethylene (for example PULPEX®) and polypropylenes, polyamides, such as nylon, polyesters such as DACRON® or Kodel®, polyurethanes, polystyrenes and the like. The fibres used can comprise only naturally occurring fibres, only synthetic fibres or any compatible combination of naturally occurring and synthetic fibres.

The fibres of the fibre material can be hydrophilic or hydrophobic, or they can comprise a combination of hydrophilic and hydrophobic fibres. The expression "hydrophilic" as used here describes fibres or surfaces of fibres which can be wetted by aqueous liquids (for example aqueous body fluids) deposited on these fibres. Hydrophilicity and wettability are typically defined in expressions of the contact angle and the surface tension of the liquids and solids involved. This is discussed in detail in a publication of the American Chemical Society entitled "Contact Angle, Wettability and Adhesion", edited by Robert F. Gould (copyright 1964). A fibre or the surface of a fibre is wetted by a liquid (that is to say it is hydrophilic) either if the contact angle between the liquid and the fibre or surface thereof is less than 90°, or if the liquid tends to distribute itself spontaneously over the surface, the two conditions usually existing simultaneously. Conversely, a fibre or the surface of a fibre is regarded as hydrophobic if the contact angle is greater than 90° and the liquid does not spread spontaneously on the surface of the fibre.

Fibres which are preferred according to the invention are hydrophilic fibres. Suitable hydrophilic fibres include cellulose fibres, modified cellulose fibres, rayon, polyester fibres, such as polyethylene terephthalate (for example DACRON®), hydrophilic nylon (HYDROFIL®) and the like. Suitable hydrophilic fibres can also be obtained by hydrophilization of hydrophobic fibres, such as thermoplastic fibres which are derived, for example, from polyolefins, such as polyethylene or polypropylene, polyacrylics, polyamides, polystyrenes, polyurethanes and the like, and are treated with a surface-active substance or treated with silica. For reasons of availability and costs, cellulose fibres, in particular pulp cellulose fibres, are preferred as the fibre material in the absorbent core (iii). Hydrophilic fibres which are furthermore preferred for use in the present invention are chemically reinforced cellulose fibres. In this context, the expression "chemically reinforced cellulose fibres" describes cellulose fibres which are reinforced by means of chemical means in order to increase the rigidity of the fibres both under dry and under aqueous conditions. Such means can include the addition of a chemical reinforcing agent which, for example, covers and/or impregnates the fibres. Such a means can also include reinforcing of the fibres by changing the chemical structure, for example by crosslinking of polymer chains. Polymer reinforcing agents which can cover or impregnate the cellulose fibres include: cationic starches which have nitrogen-containing groups (for example amino groups), such as are obtainable from National Starch and Chemical Corp., Bridgewater, N.J., USA, latexes, wet-resistant resins, such as polyamide-epichlorohydrin resin (for example Kymene 557H, Hercules, Inc., Wilmington, Del., USA), polyacrylamide resins, such as are described, for example, in U.S. Pat. No. 3,556,932, commercially obtainable polyacrylamides, such as Parex® 631 NZ from American Cyanamid Co., Stanfort, Conn., USA, urea-formaldehydes and melamine-formaldehyde resins. Fibres which have been reinforced by crosslinking bonds in individual forms (that is to say the individual reinforced fibres and the processes for their preparation) are described, for example, in U.S. Pat. No. 3,224,926, U.S. Pat. No. 3,440,135, U.S. Pat. No. 3,932,209 and in U.S. Pat. No. 4,035,147. Preferred crosslinking agents are glutaraldehyde, glyoxal, formaldehyde, glyoxalic acid, oxydisuccinic acid and citric acid. The cellulose fibres reinforced by crosslinking or coating, impregnation or crosslinking can be twisted or crimped, and the fibres are preferably twisted and additionally crimped.

All the fibres which are mentioned as thermoplastic fibres in DE 695 21 888 T2 on page 59 et seq. can furthermore be employed as the fibre material. According to a particular embodiment of the dehydratable hygiene articles according to the invention, the absorbent core comprises, in addition to the superabsorbent material, cellulose fibres and two-component fibres, in particular so-called shell/core fibres of polyethylene and polypropylene, polyethylvinyl acetate and polypropylene, polyethylene and polyester, polypropylene and polyester or copolyester and polyester. Particularly preferred two-component fibres are in turn those two-component fibres which are mentioned as two-component fibres in DE 695 21 888 T2.

In a particular embodiment of the absorbent core (iii), this comprises, in addition to the substrate and the superabsorbent material, further pulverulent substances, such as, for example, odour-binding substances, such as cyclodextrins, zeolites, inorganic or organic salts and similar materials. It is furthermore preferable according to the invention for the absorbent core (iii) to have at least one region in which the amount of superabsorbent material is in a range of from 10 to 100 wt. %, preferably in a range of from 20 to 95 wt. % and particularly preferably in a range of from 50 to 90 wt. %, based on the region, this region preferably having a size of at least 0.001 $mm^3$, particularly preferably of at least 0.01 $mm^3$, more preferably of at least 0.1 $mm^3$ and most preferably of at least 0.3 $mm^3$.

The structure and the further components optionally contained in the absorbent core (iii) corresponds to the structure and, respectively, correspond to the components disclosed in DE 695 21 888 T2 in connection with the "absorbent cores" disclosed there. The disclosure content of DE 695 21 888 T2 with respect to the structure of the "absorbent element" is introduced herewith as reference and forms part of the disclosure of the present invention.

The fibrous or particulate superabsorbent materials can be distributed homogeneously in the fibre materials, they can be incorporated in layer form between the fibre material, or the concentration of the superabsorbent materials can have a gradient within the fibre material.

The absorbent core (iii) can be produced by conventional processes known to the person skilled in the art, such as are generally called collectively by the person skilled in the art drum forming, with the aid of forming wheels, forming pockets and product forming and appropriately matched metering equipment for the raw materials. In addition, modern, established processes, such as the so-called airlaid process (e.g. EP-A-0 850 615, U.S. Pat. No. 4,640,810) with all forms of metering, laying down of the fibres and bonding, such as hydrogen bonding (e.g. DE-A-197 50 890), thermobonding, latex bonding (e.g. EP-A-0 850 615) and hybrid bonding, the so-called wetlaid process (e.g. WO-A-99/49905), carding, meltblown, spun-blown processes and similar processes for the production of absorbent nonwovens (in the context of the definition of EDANA, Brussels), also in combinations of these processes with one another, are conventional methods for the production of the absorbent core (iii). Possible further processes are the production of laminates in the broadest sense and of extruded and coextruded, wet- and dry-bonded and subsequently bonded structures.

In a further embodiment of the absorbent core (iii), this comprises, in addition to the substrate (=fibre material) and the superabsorbent material incorporated into the substrate, which together serve as the storage layer for the body fluids, an absorption layer (v) which preferably serves for rapid absorption and distribution of the liquid in the absorbent core (iii). In this context, the absorption layer (v) can be arranged directly over the storage layer, but it is also possible for the absorption layer (v) to be separated from the storage layer by an intermediate layer (vi) which is preferably stable to liquids. This intermediate layer (vi) then primarily serves as a support substrate for the absorption layer (v) and the storage layer. Preferred materials for this intermediate layer (vi) are polyester spunbonded nonwovens, or nonwovens of polypropylene, polyethylene or nylon. In one embodiment of the absorbent core (iii), the absorption layer (v) is free from superabsorbent material. The absorption layer (v) can have any suitable size and does not have to extend over the entire length or width of the storage layer. The absorption layer (v) can be constructed, for example, in the form of a strip or patch. The total absorption layer (v) is preferably hydrophilic, but it can also have hydrophobic components. The absorption layer (v) can comprise a woven material, a nonwoven material or another suitable type of a material. Preferably, the absorption layer (v) is based on hydrophobic polyethylene terephthalate fibres (PET fibres), chemically reinforced cellulose fibres or on mixtures of these fibres. Materials which are further suitable are polypropylene, polyethylene, nylon or biological fibres. If the absorption layer (v) comprises a nonwoven material, it can be produced by a large number of different processes. These include wet laying, application in a stream of air, application in the melt, formation as a spunbonded nonwoven and carding (this include thermal bonding, bonding with solvents or bonding by the melt spinning process). The processes mentioned last (formation as a spunbonded nonwoven and carding) are preferred if alignment of the fibres in the absorption layer (v) is desired, since in such processes it is easier to align the fibres in a single direction. A PET spunbonded nonwoven is a particularly preferred material for the absorption layer (v).

The absorbent core (iii) is furthermore preferably characterized by a weight per unit area of at least 0.03 g/cm$^2$, preferably of at least 0.06 g/cm$^2$, particularly preferably in the range of from 0.03 to 0.12 g/cm$^2$ and more preferably in the range of from 0.06 to 0.12 g/cm$^2$, the absorbent core (iii) moreover having a thickness of a maximum of about 20 mm, preferably a maximum of about 15 mm and more preferably a maximum of about 10 mm. The area of the absorbent core (iii) is preferably a maximum of about 2,500 cm$^2$, particularly preferably a maximum of about 1,000 cm$^2$ and more preferably a maximum of about 500 cm$^2$.

According to a preferred embodiment of the dehydratable nappy according to the invention, the lower layer (i) which is impermeable to aqueous liquids, the upper layer (ii) which is permeable to aqueous liquids and the absorbent core (iii) are arranged as is shown in EP-A-0 802 776 in FIG. 1 for the top sheet described there which is impermeable to liquid, the top sheet which is permeable to liquid and the absorbent core. In this context, the upper layer (ii), which comes into contact with the skin of the wearer of the nappy, is joined to the lower layer (i) along the circumference of the lower layer (i). The absorbent core (iii), which is preferably likewise joined to the lower layer (i), is arranged between the layers (i) and (ii). By this arrangement of the components, a nappy under-side which faces away from the nappy wearer, a nappy upper side which comes into contact with the skin of the nappy wearer when the nappy is worn, and, due to the finite thickness of the absorbent core (iii) enclosed by the upper layer (ii) and the lower layer (i), a side edge, which extends in the longitudinal direction of the absorbent core (iii) are formed. The height of this side edge increases when aqueous liquids penetrate through the permeable upper layer (ii) into the absorbent core (iii) and cause swelling thereof.

The dehydratable hygiene articles according to the invention comprise as a further component a trigger system (iv) comprising a superabsorbent material (a) which is capable of absorbing aqueous liquids with the formation of a hydrogel, it being possible, after the trigger system has been activated, for at least some of the aqueous liquid absorbed to be released from the superabsorbent material (a) when this is present as a hydrogel. In this context, it is preferable for the "centrifuge retention capacity", determined in accordance with ERT 441.2-02 (in the case of a particulate superabsorbent material (a), determined for the total particle fraction), of the superabsorbent material to be reduced by at least 20%, preferably by at least 40% and most preferably by at least 60% within 120 minutes, preferably within 60 minutes and more preferably within 30 minutes of the trigger system being activated.

In the context of the invention, a "trigger system" is preferably understood as meaning a system which can in principle be present in two different states, it being possible for the system to be converted from the one of the at least two different states into the other of the at least two different states by a targeted measure acting on the trigger system.

In connection with the trigger system, it is furthermore preferable for the content of "extractables", determined in accordance with ERT 470.2-02, in the superabsorbent material (a) to increase by less than 50%, preferably less than 35%, more preferably by less than 20% and most preferably by less than 10% within 30 minutes, preferably within 60 minutes and more preferably within 120 minutes of the trigger system being activated.

According to a first particular embodiment of the dehydratable hygiene articles according to the invention, the trigger system (iv) comprises an anionic superabsorbent material (a), the absorption properties of which depend on the pH, and an acidic material (c) present spatially separated from the superabsorbent material (a), the trigger system being activated when it is made possible for the acidic material (c) to come into contact with the hydrogel.

Preferred anionic superabsorbent materials are polymers which are based on (α1) 20-99.999 wt. %, preferably 55-98.99 wt. % and particularly preferably 70-98.79 wt. % of polymerized, ethylenically unsaturated, acid group-containing monomers or salts thereof or polymerized, ethylenically unsaturated monomers containing a protonated or quaternized nitrogen, or mixtures thereof, mixtures containing at least ethylenically unsaturated, acid group-containing monomers, preferably acrylic acid, being particularly preferred, (α2) 0-80 wt. %, preferably 0-44.99 wt. % and particularly preferably 0.1-44.89 wt. % of polymerized, monoethylenically unsaturated monomers which can be copolymerized with (α1), (α3) 0.001-5 wt. %, preferably 0.01-3 wt. % and particularly preferably 0.01-0.5 wt. % of one or more crosslinking agents, (α4) 0-30 wt. %, preferably 0-5 wt. % and particularly preferably 0.1-5 wt. % of a water-soluble polymer, (α5) 0-20 wt. %, preferably 2.5-15 wt. % and particularly preferably 3-6 wt. % of water and (α6) 0-20 wt. %, preferably 0-10 wt. % and particularly preferably 0.1-8 wt. % of one or more auxiliary substances, the sum of the amounts by weight (α1) to (α6) being 100 wt. %.

With respect to the preferred components (α1) to (α6) and with respect to the nature and manner of the preparation of these polymers, reference is made to WO-A-2004/037903, the disclosure of which is introduced herewith as reference.

Anionic superabsorbent materials which are preferred according to the invention are crosslinked polymers which are based to the extent of at least 50 wt. %, preferably to the extent of at least 70 wt. % and more preferably to the extent of at least 90 wt. % on monomers containing carboxylate groups. It is furthermore preferable according to the invention for the monomer containing carboxylate groups to comprise acrylic acid to the extent of at least 50 wt. %, preferably to the extent of at least 70 wt. %, this preferably being neutralized to the extent of at least 20 mol %, particularly preferably to the extent of at least 50 mol % and more preferably in a range of from 60 to 85 mol %.

Ir is particularly preferable according to the invention, in the case of this first particular embodiment of the dehydratable hygiene article according to the invention, for the anionic superabsorbent material (a) to be a crosslinked polyacrylate in particulate form which has been obtained by polymerization of an acrylic acid, which is optionally already partly neutralized, in the presence of one of the crosslinking agents mentioned in WO-A-2004/037903 in aqueous solution containing the acrylic acid in an amount in a range of from 5 to 80 wt. %, preferably 10 to 70 wt. % and particularly preferably 20 to 50 wt. %, based on the weight of the aqueous solution, and subsequent comminution of the hydrogel obtained, drying of the comminuted hydrogel to a water content in a range of from 1 to 50 wt. %, preferably 2.5 to 40 wt. % and particularly preferably 5 to 30 wt. %, and optionally further grinding of the dried hydrogel.

In addition to this anionic superabsorbent material (a), the trigger system in this first particular embodiment of the hygiene article according to the invention comprises an acidic material (c) present spatially separated from the superabsorbent material (a). In this context, "present spatially separated" means that the acidic material (c) is arranged in the dehydratable hygiene article such that it can come into contact with the anionic superabsorbent material (a) only after the trigger system has been activated, for example by a defined mechanical action on the hygiene article.

Any organic or inorganic acid known to the person skilled in the art can be employed as the acidic material (c). Preferably, an organic, preferably pulverulent material is employed as the acidic material (c), for example a material chosen from the group including lactic acid, glutaric acid, aspartic acid, malonic acid, adipic acid, amino acids, citric acid, benzoic acid, fumaric acid, maleic acid or oxalic acid. Liquid acidic materials, such as, for example, dilute formic acid, dilute acetic acid or dilute hydrochloric acid, can also be employed instead of or also in addition to these organic, preferably pulverulent acidic materials.

According to a particularly preferred embodiment of this first variant of the hygiene article according to the invention, the superabsorbent material (a) is a crosslinked, partly neutralized polyacrylate and the acidic material (c) is citric acid.

The spatial separation of the anionic superabsorbent material (a) and the acidic material (c) in the hygiene article according to the invention is preferably achieved by incorporating the anionic superabsorbent material (a) as a superabsorbent material into the absorbent core (iii) by the method and manner described above, while the acidic material (c) is accommodated spatially separated from the absorbent core (iii), it being necessary for the spatial separation to be such that the acidic material (c) cannot readily come into contact with the anionic superabsorbent material (a), especially when the nappy is in contact with body fluids. For this, the acidic material (c) is preferably incorporated into a capsule and one or more of these capsules are incorporated, for example, into the absorbent core (iii) or into the absorption layer (v) if the hygiene article is a nappy which has such an absorption layer. The capsule can furthermore be arranged, for example, on the side of the lower layer (i) facing the absorbent core (iii). In principle, the capsule can be arranged in any conceivable region of the hygiene article as long as it is ensured that the absorption properties of the hygiene article are not noticeably impaired by the presence of the capsule or capsules and that after destruction of the capsule the acidic material (c) can come into contact with the anionic superabsorbent material (a).

The capsule is preferably a capsule which can be influenced in its integrity a1) by mechanical action,
a2) by thermal action,
a3) by electromagnetic irradiation or
a4) by chemical changes such that the acidic material (c) can be released from the capsule, it also being possible for this release to take place with a time delay after the start of the actions according to a1) or a2) or after the start of an electromagnetic irradiation or a chemical change according to a3) or a4). The capsules can be, for example, spherical particles of a thermoplastic material, capsules of plastic which are easily breakable, capsules of a material which is sensitive to electromagnetic radiation, in particular to UV radiation, or also paper-thin glass bodies. The capsules can moreover not only have a spherical shape, but can also be constructed, for example, in tubular form. It would furthermore be conceivable for the acidic material (c) to be introduced, for example, into a tube of plastic closed at one end, over which is tucked a second tube of plastic, likewise closed at one end. In this case the trigger system could be activated in a manner such that, if the tube filled with the acidic material (c) is arranged, for example, in the longitudinal direction relative to the absorbent core (iii) in a dehydratable nappy according to the invention, the nappy is drawn apart in the longitudinal direction of the absorbent core (iii) such that the two tubes of plastic tucked over one another are pulled away from one another in opposite directions, so that the acidic material (c) can now come into contact with the anionic superabsorbent material (a) in the absorbent core (iii).

In addition to encapsulation of the acidic material (c), this can also be present separated from the anionic superabsorbent material (a) by an individual membrane in that, for example, the lower layer (i) has depressions into which the acidic material (c) is introduced, these depressions subsequently being closed with a material which, like the capsule material described above, can easily be destroyed by mechanical, thermal or electromagnetic influences.

The amount of acidic material (c) relative to the amount of anionic superabsorbent material (a) is preferably chosen such that after the trigger system (iv) has been activated, the degree of neutralization of the superabsorbent material (a) is reduced by at least 10 mol %, preferably at least 20 mol %, still more preferably at least 30 mol %, more preferably at least 40 mol % and most preferably by at least 50 mol %. Thus, if a partly neutralized, crosslinked polyacrylate having a degree of neutralization of 70 mol % is employed as the superabsorbent material (a), the amount of acidic material (c) provided is such that after the trigger system (iv) has been activated, the degree of neutralization is reduced to at most 60 mol %, preferably at most 50 mol %, still more preferably at most 40 mol %, more preferably at most 30 mol % and most preferably at most 20 mol %. In the case of an anionic superabsorbent material (a), a degree of neutralization of X mol % means that X mol % of the acid groups present in the superabsorbent material (a) are present in the form of the corresponding base.

According to a second particular embodiment of the dehydratable hygiene articles according to the invention, the trigger system (iv) comprises a cationic superabsorbent material (a), the absorption properties of which depend on the pH, and a basic material (d) present spatially separated from the superabsorbent material (a), the trigger system being activated when it is made possible for the basic material (d) to come into contact with the hydrogel.

Crosslinked polymers which are based on ethylenically unsaturated monomers containing a quaternized nitrogen are preferred as the cationic superabsorbent material (a). Monomers which are preferred in this connection are dialkylammoniumalkyl(meth)acrylates in quaternized form, for example trimethylammoniumethyl(meth)acrylate methosulphate or dimethylethylammoniumethyl(meth)acrylate ethosulphate, and (meth)acrylamidoalkyldialkylamines in quaternized form, for example (meth)acrylamidopropyltrimethylammonium chloride, trimethylammoniumethyl(meth)acrylate chloride or (meth)acrylamidopropyltrimethylammonium sulphate. Preferred cationic water-absorbing materials are furthermore crosslinked polyamines, polyvinylamines, polyallylamines, polyethyleneimines or polydiallyldimethylammonium chloride, or natural cationic polymers, such as partly deacetylated chitin, chitosan and chitosan salts.

Any organic or inorganic base known to the person skilled in the art can be employed as the basic material (d). Preferably, an inorganic pulverulent material, for example a material chosen from the group including sodium carbonate, sodium bicarbonate, ammonium carbonate or sodium hydroxide, is employed as the basic material (d). Aqueous basic solutions, such as, for example, dilute sodium hydroxide solution or soda water, can also be employed instead of or also in addition to these inorganic pulverulent basic materials.

The spatial separation of the cationic superabsorbent material (a) from the basic material (d) is preferably effected in the same manner described above in which the spatial separation of the anionic superabsorbent material (a) from the acidic material (c) is also realized.

The amount of basic material (d) relative to the amount of cationic superabsorbent material (a) is preferably chosen such that after the trigger system (iv) has been activated, the degree of neutralization of the superabsorbent material (a) is reduced by at least 10%, preferably at least 20%, still more preferably at least 30%, more preferably at least 40% and most preferably by at least 50%. In the case of a cationic superabsorbent material (a), a degree of neutralization of X mol % means that X mol % of the base groups present in the superabsorbent material (a) are present in the form of the corresponding acid.

According to a third particular embodiment of the dehydratable hygiene articles according to the invention, the trigger system (iv) comprises, in addition to the superabsorbent material (a), a preferably neutral salt (e) present spatially separated from the superabsorbent material (a) or a preferably neutral salt solution (f) present spatially separated from the superabsorbent material (a), the trigger system being activated when it is made possible for the salt (e) or the salt solution (f) to come into contact with the hydrogel.

Contact of neutral salts with a swollen superabsorbent material can also lead to dehydration. For example, if neutral salts of monovalent cations are employed, such as, for example, NaCl, the osmotic pressure is the driving force for shrinking of the superabsorbent material. On the other hand, if salts of multivalent cations, such as, for example, aluminium salts, are employed as neutral salts in combination with anionic superabsorbent materials, the crosslinking of the anionic groups by the multivalent cations above all is the driving force for shrinking of the superabsorbent material.

In this particular embodiment of the dehydratable hygiene articles according to the invention, the crosslinked, partly neutralized polyacrylates described above in connection with the anionic superabsorbent material (a) are preferably employed as the superabsorbent material (a).

A "neutral salt" in the context of the present invention is preferably understood as meaning salts which contain no $H^-$ ion as the cation and also no anions chosen from the group consisting of $OH^-$ ions, $CO_3^{2-}$ ions, $HCO_3^-$ ions and anions of organic acids, such as, for example, acetate or lactate ions. In this connection, it is preferable for the cation of the neutral salt to have a $pK_a$ value of at least 2, particularly preferably at least 4, still more preferably at least 6 and most preferably at least 8, while the anion of the neutral salt has a $pK_b$ value of at least 6, particularly preferably at least 8, still more preferably at least 10 and most preferably at least 12. These "neutral salts" are preferably salts containing a metal cation and anions chosen from the group consisting of chloride, bromide, iodide, sulphate, sulphite, nitrate or nitrite. The term "neutral salt" as used herein therefore certainly includes salts which contain no $H^+$ ion as the cation and also no anions chosen from the group consisting of $OH^-$ ions, $CO_3^{2-}$ ions, $HCO_3^-$ ions and anions of organic acids, but which nevertheless lead to a pH which differs from 7.0 when dissolved in water, such as, for example, $FeCl_3$. Neutral salts which are preferred according to the invention include salts of which the cations are chosen from the group consisting of $Na^+$, $K^+$, $Li^+$, $Ca^{2+}$, $Mg^{2+}$, $Al^{2+}$, $Fe^{2+}$, $Fe^{3+}$, $Zn^{2+}$, $Cu^+$ and $Cu^{2+}$, and of which the anions are chosen from the group consisting of $Cl^-$, $Br^-$, $I^-$, $SO_4^{2-}$, $HSO_4^-$, $NO_3^-$, $NO_2^-$, $HPO_4^{2-}$ and $H_2PO_4^-$, wherein the anions and the cations can be combined with one another as desired. Salts which contain mixtures of at least two of the abovementioned cations and/or mixtures of at least two of the abovementioned anions are also conceivable as neutral salts.

Particularly preferred neutral salts (e) are chosen from the group consisting of polyvalent salts, such as calcium chloride, magnesium chloride, iron(II) chloride, iron(III) chloride, aluminium chloride, calcium sulphate or aluminium sulphate, or also monovalent salts, such as sodium chloride, potassium chloride and lithium chloride, polyvalent, in particular di- or trivalent salts being most preferred.

The amount (based on the cations) of preferably di- or trivalent salt (e) in the hygiene article according to the invention, based on the anionic groups in the superabsorbent material (a), preferably based on the carboxylate groups in the superabsorbent material (a) based on partly neutralized polyacrylates, is preferably in a range of from 0.1 to 1 mol of cations per mol of anionic groups, preferably in the range of from 0.25 to 0.75 mol of cations per mol of anionic groups and most preferably in the range of from 0.3 to 0.5 mol of cations per mol of anionic groups. If aqueous salt solutions (f) are employed, the amount of salt (e) in the aqueous salt solution (f) is preferably in a range of from 10 to 50 wt. %, particularly preferably in a range of from 15 to 40 wt. % and more preferably in a range of from 20 to 30 wt. %.

Here also, the spatial separation between the salt (e) or the aqueous salt solution (f) and the superabsorbent material (a) is preferably effected by the method and manner such as has already been described with respect to the spatial separation between the anionic superabsorbent material (a) and the acidic material (c) in connection with the first particular embodiment of the hygiene articles according to the invention.

In addition to the abovementioned components, the dehydratable hygiene article according to the invention can also comprise further components. If the hygiene article is a nappy, this advantageously also has closures which can be used to fix the nappy around the waist of the wearer. Suitable closures include Velcro-like closures, adhesive tape closures, buttons, press-studs, mushroom and loop closures and the like. In the case of a nappy, the hygiene articles can furthermore comprise elastic leg tapes which prevent excreted body fluids from running out of the nappy.

It is furthermore preferable according to the invention for the dehydratable hygiene article to have in the lower layer (i) which is impermeable to aqueous liquids and/or in the upper layer (ii) which is permeable to aqueous liquids a closed outlet which can be opened and via which, after opening, the aqueous liquid at least partly released after the trigger system (iv) has been activated can be removed from the hygiene article. In this context, in the case of a nappy as the hygiene article the outlet is located centrally in the walking region in the lower layer (i) which is impermeable to aqueous liquids. However, it is also conceivable to locate the outlet in the region of the abovementioned side edge.

Preferably, the outlet is a hole in one of the two layers (i) or (ii) which preferably has a diameter of at least 0.5 cm, particularly preferably at least 1.0 cm and more preferably at least 2.0 cm. In the still unused hygiene article, this outlet is preferably closed by the hole being closed by means of an adhesive strip which, after the hygiene article has been used, can be at least partly pulled off in order to open the outlet. The outlet can furthermore be constructed such that one of the two layers (i) or (ii) has a perforated region which can be torn open after the hygiene article has been used. In the simplest case, such an outlet comprises a perforated line, for example, located in the lower layer (i) which is impermeable to liquids. After the hygiene article has been used, the lower layer (i) is torn apart in the region of this perforated line, so that the liquid released after the trigger system has been activated can exit through the gap formed. Such a perforated region can advantageously also be located in the side edge of a nappy. In addition to perforation of particular regions, it is also advantageous to incorporate tear-open threads into individual layers.

A contribution towards achieving the abovementioned objects is also made by a method for dehydrating a hygiene article, comprising the method steps:
a. activation of the trigger system (iv) in a dehydratable hygiene article according to the invention which has absorbed aqueous liquid,
b. removal from the hygiene article of at least some of the aqueous liquid absorbed which is at least partly released after the trigger system (iv) has been activated.

Preferably, the hygiene article is a nappy. According to the method according to the invention, it is furthermore preferable for the removal, in step b, from the hygiene article of at least some of the aqueous liquid absorbed which is at least partly released after the trigger system (iv) has been activated to be carried out by compressing the hygiene article, preferably by loading the hygiene article with a pressure which is greater than the atmospheric pressure surrounding the hygiene article, or by wringing out the hygiene article. According to another embodiment of the method according to the invention, the removal is carried out by the action of a centrifugal force or by evaporation of at least some of the liquid released.

Preferably, the removal of the liquids released is carried out at the earliest 5 minutes, particularly preferably at the earliest 30 minutes and more preferably at the earliest 60 minutes after the trigger system has been activated.

If the dehydratable hygiene article according to the invention has the outlet described above, it is preferable for this outlet to be opened only immediately before the removal of the liquid released.

A further contribution towards achieving the abovementioned objects is made by a device for dehydrating a dehydratable hygiene article comprising a superabsorbent material (a), which comprises the device constituents:
A) a container having
  A1) a first opening via which a dehydratable hygiene article which has absorbed aqueous liquids can be introduced into the container A),
  A2) a device constituent for driving out of the hygiene article the aqueous liquid released,
  A3) a closable second opening positioned in the lower third of the device, via which the aqueous liquids released can exit from the container A),
B) optionally a trigger element which renders it possible, after activation thereof, for at least some of the aqueous liquid absorbed to be released from the superabsorbent material (a) when this is present as a hydrogel, and
C) optionally a device constituent with which an opening can be introduced into the hygiene article.

The container A) is preferably a bucket or another vessel open at the top, for example also a toilet, into which aqueous liquids can be filled. The container preferably has a height in a range of from 20 cm to 150 cm, particularly preferably in a range of from 30 cm to 100 cm and a diameter in a range of from 10 cm to 100 cm, particularly preferably in a range of from 30 cm to 80 cm. It is furthermore preferable for the container to be produced from a material of plastic with a wall thickness in a range of from 0.5 mm to 10 mm.

The first opening A1) of the container A) is preferably the entire cross-section in the upper region of the container. However, it is also possible to employ a container with a cover, an optionally closable opening through which the swollen hygiene article can be introduced into the container preferably being positioned centrally in the cover.

The device constituent A2) for driving out the aqueous liquid released is preferably a press or a centrifuge. A nappy refuse press such as is known, for example, from DE 296 07 480 U1 can furthermore be employed for this purpose.

The closable second opening A3) accommodated in the lower third, preferably in the lower quarter and particularly preferably in the base region of the device, via which the aqueous liquids released can exit from the container A) is preferably a shut-off valve. This opening can optionally have a fluid-carrying connection to a sewerage system.

According to a particular embodiment of the device according to the invention, this furthermore comprises a tray which is arranged at least 1 cm, preferably at least 5 cm above the base of the container A) parallel to the base, has holes and preferably extends over the entire base region. The swollen hygiene articles are deposited on this tray. If the liquid absorbed is now removed from the hygiene article by actuating the device constituent A2), the liquid released runs through the tray in the direction of the base of the container A), from which it can then be removed after the outlet A3) has been opened.

According to another embodiment of the device according to the invention, the container A) is constructed such that it has an adapter in the base region, by means of which the container can be placed on an opened toilet. The base region in this case furthermore has a further closable opening. If the dehydratable hygiene articles according to the invention are now introduced into the device after the trigger system (iv) has been activated, after the device constituent A2) has been actuated the liquid released runs directly through the opening in the base into the toilet.

It is furthermore preferable in the device according to the invention for this to have in the inside of the container A) a trigger element B) which renders it possible, after activation thereof, for at least some of the aqueous liquid absorbed to be released from the superabsorbent material (a) when this is present as a hydrogel.

If the swollen hygiene article is a hygiene article according to the first, second or third particular embodiment and this contains an encapsulated material (acidic or basic materials or salts), those devices with which the encapsulated material can be released are possible as the trigger element. If a material which is sensitive to electromagnetic radiation, in particular to UV radiation is employed as the capsule material, a corresponding source of radiation is possible as the trigger element B).

It may furthermore be preferable according to the invention for the device to have a further device constituent with which an opening can be introduced into the hygiene article. In this manner, the outflow from the hygiene article of the liquid released can be facilitated. All punching devices with which holes can be punched into the hygiene article, preferably holes in one of the two layers i) or ii) or continuous holes through the entire hygiene article, are possible in principle.

Preferably, the device according to the invention is used for dehydrating the hygiene articles according to the invention, it being particularly preferable for the second opening A3) to have a fluid-carrying connection to a sewerage system.

A contribution towards achieving the abovementioned objects is also made by a kit comprising
- a device according to the invention for dehydrating a hygiene article and one or more dehydratable hygiene articles according to the invention,
or
- one or more dehydratable hygiene articles according to the invention and, present separated from the hygiene article, a trigger component,
or
- a device according to the invention for dehydrating a hygiene article and a trigger component,
or
- a device according to the invention for dehydrating a hygiene article, a dehydratable hygiene article according to the invention and, present separated from the hygiene article, a trigger component.

The trigger component is preferably a material which, when it comes into contact with the superabsorbent material (a) in the hygiene article, is capable of reducing the "centrifuge retention capacity", determined in accordance with ERT 441.2-02 (in the case of a particulate superabsorbent material (a), determined for the total particle fraction), by at least 10%, particularly preferably by at least 25%, still more preferably by at least 50% and most preferably by at least 70%.

Preferably, the trigger component is chosen from the group consisting of an acidic material (c), a basic material (d), a salt (e) or a salt solution (f). Preferred acidic materials, basic materials or neutral salts or salt solutions are those compounds and solutions which have already been mentioned in connection with the second, third and fourth particular embodiment of the dehydratable hygiene articles according to the invention.

The invention will now be explained in more detail with the aid of non-limiting figures.

DESCRIPTION OF THE INVENTION

Figure 1:
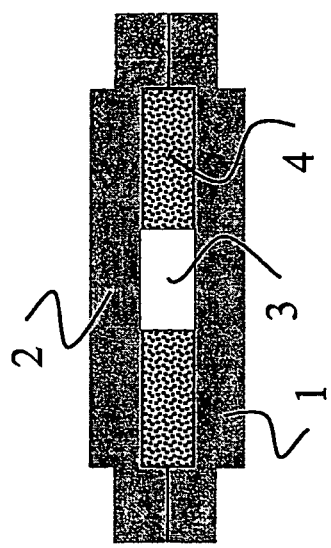
FIG. 1 shows a hygiene article according to the invention in the form of a nappy in cross-section at the level of the line A shown in FIG. 2.
Figure 2:
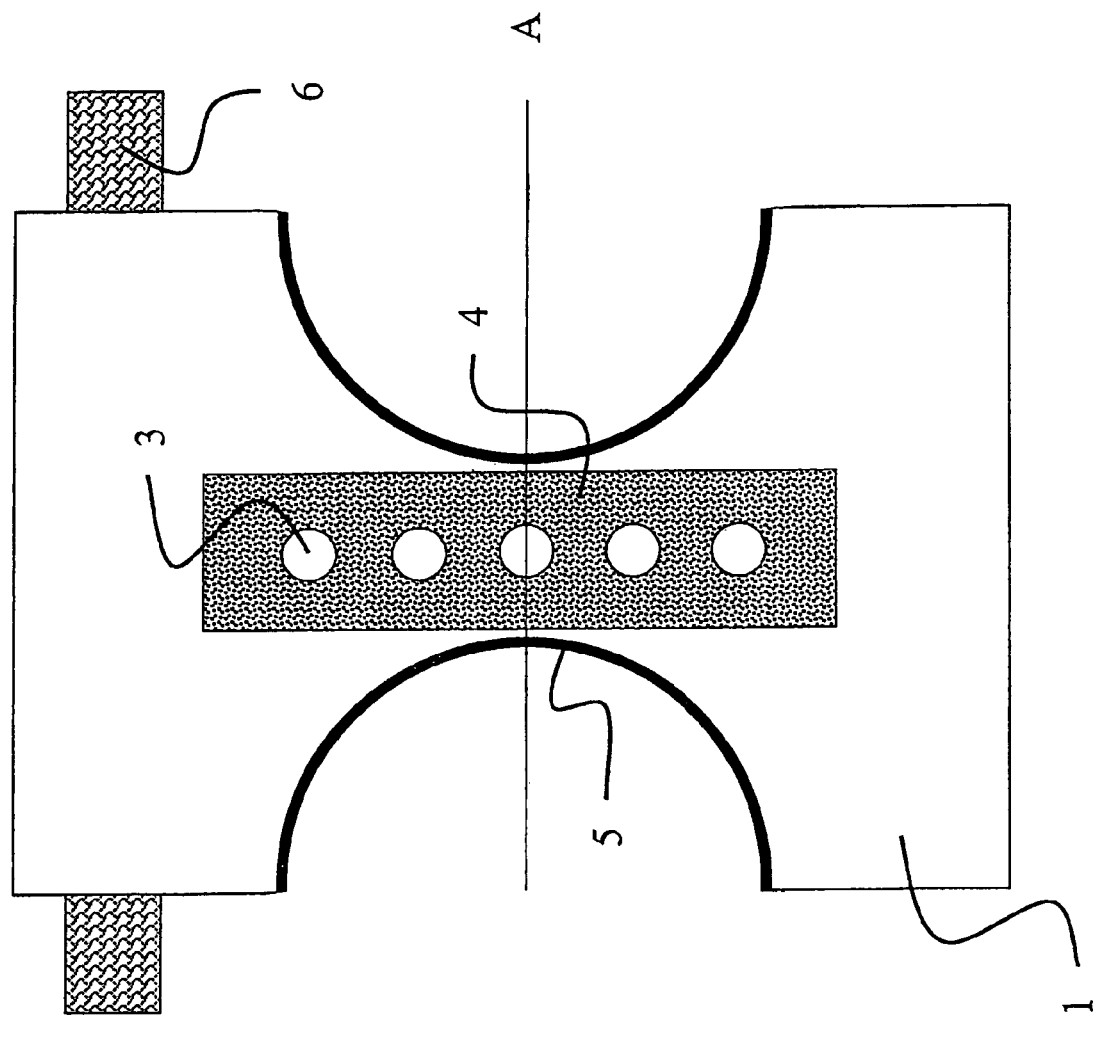
FIG. 2 shows a hygiene article according to the invention in the form of a nappy from the top.
Figure 3:
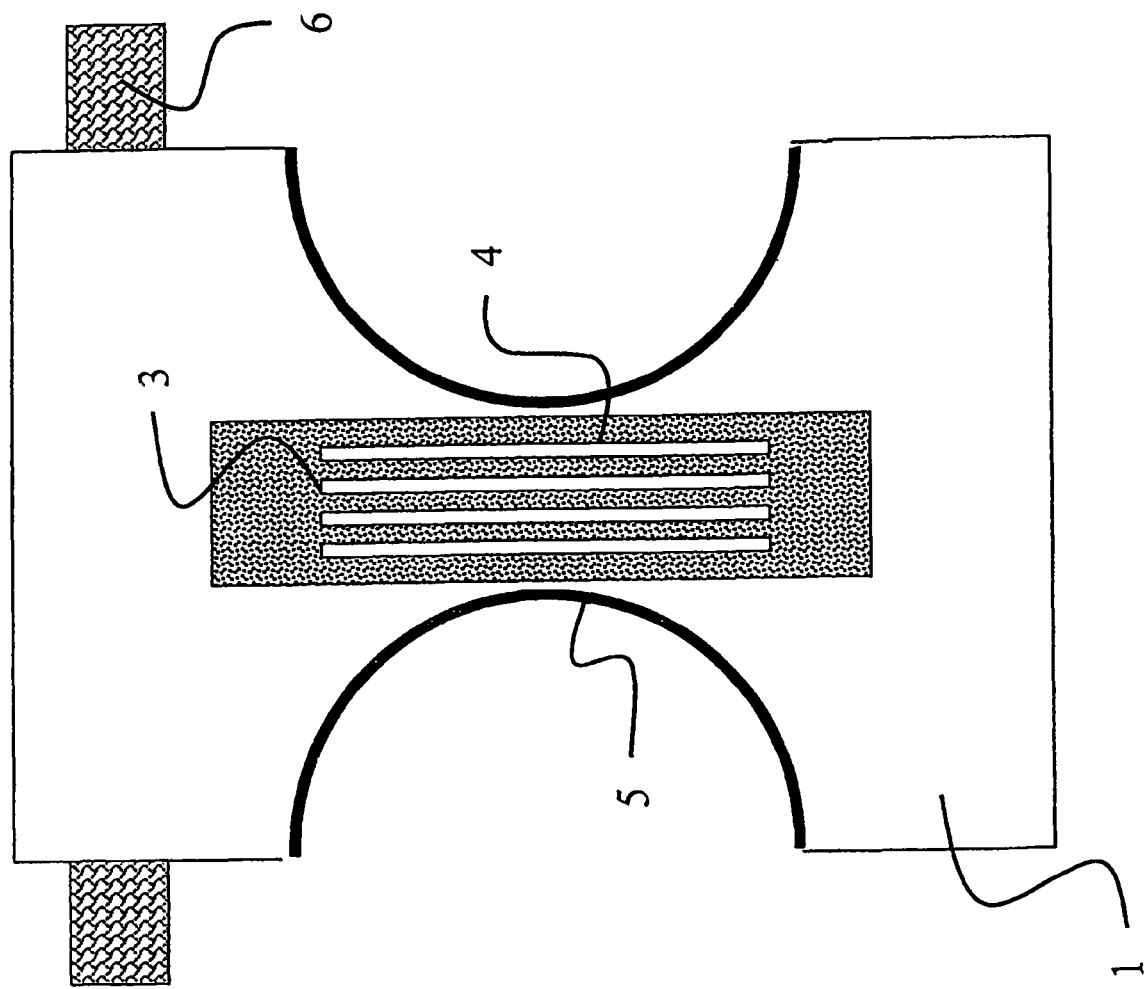
FIG. 3 shows another hygiene article according to the invention in the form of a nappy from the top.

As can be seen from FIGS. 1, 2 and 3, the hygiene article according to the invention comprises a lower layer 1 which is impermeable to aqueous liquids, an upper layer 2 which is permeable to aqueous liquids and a core 4 which is arranged between the lower and the upper layer 1 and 2 respectively and absorbs aqueous liquids. This absorbent core 4 preferably comprises a fibre material and superabsorbent polymer particles. In this context, the absorbent core preferably extends over that region of the lower layer 1 (this is facing away from the body side when the nappy is worn) which is in the walking region when the nappy is worn. The nappy furthermore has closures 6 and elastic leg tapes 5.

In the dehydratable nappy according to the invention shown in FIG. 2, spherical capsules 3 which contain neutral salts or acidic or basic materials are introduced in the region of the absorbent core 4. If the capsules are destroyed, for example by mechanical action, the encapsulated materials come into contact with the superabsorbent material in the absorbent core 4, so that shrinking of the superabsorber occurs. The liquid released can exit from the hygiene article, for example, via the permeable upper layer 2. The trigger system in the nappy shown in FIG. 2 accordingly comprises the superabsorbent material contained in the absorbent core 4 and the capsules 3. It is also conceivable for the hygiene article to have closable outlets (not shown), through which liquids can exit.

According to FIG. 3, the dehydratable nappies according to the invention can comprise a component which influences the absorption capacity of the superabsorbent material, such as, for example, an acidic, basic or a neutral salt, also in the form of longitudinally extended tubes 3. It is also conceivable for this component to be integrated into the lower layer (i) which is impermeable to aqueous liquids and/or the upper layer (ii) which is permeable to aqueous liquids or to be connected in another form to one of these two layers or to both layers.

Figure 4:
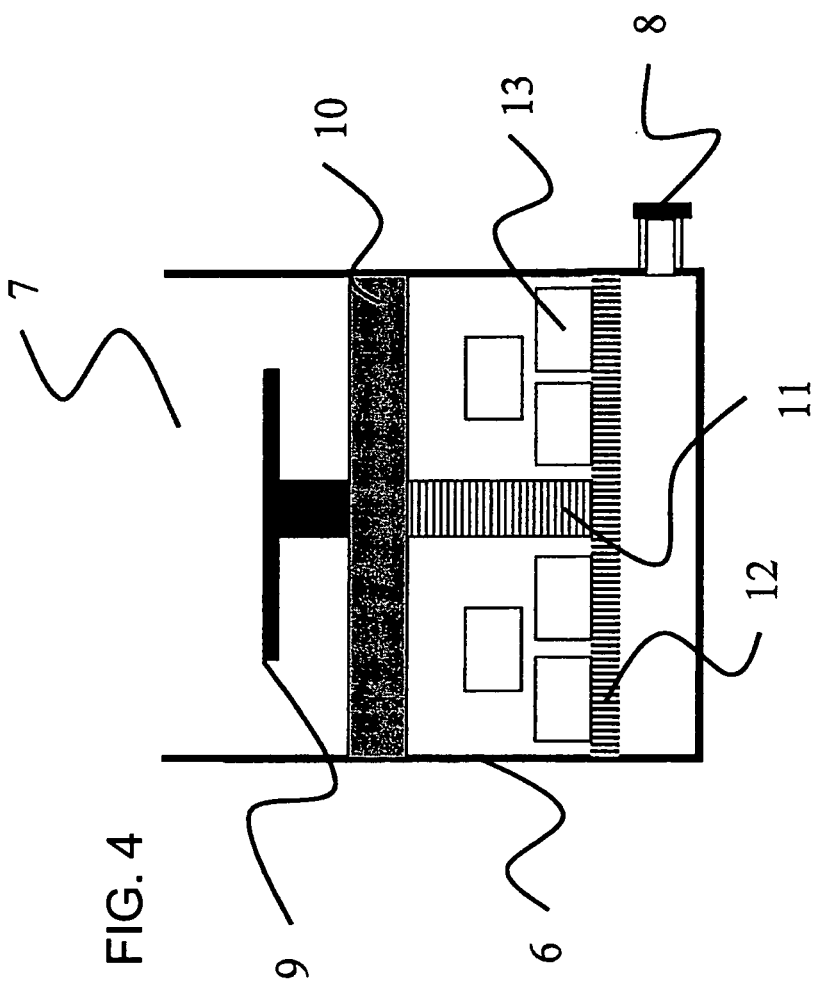
FIG. 4 shows a device according to the invention for dehydrating a hygiene article.

The device according to the invention for dehydrating a swollen hygiene article comprises a container 6, which preferably has the form of a bucket (see FIG. 4). In the embodiment shown in FIG. 4, the container is open at the top, so that used hygiene articles 13 can be introduced into the container 6 via the opening 7. The container advantageously has a perforated tray 12, on which the hygiene articles 13 are laid. By means of a suitable pressing device, which in the embodiment of the device according to the invention shown in FIG. 4 is a stamp 10 which can be pressed by means of a threaded screw 11 and a rotary knob 9 in the direction of the tray 12, the nappies can be compressed. When the hygiene articles 13 are compressed between the stamp 10 and the tray 12, the liquid absorbed (provided that the trigger system has been activated beforehand) passes through the holes of the tray 12 and arrives in the region of the base of the container 6. The liquid released can be removed from the device via the outlet 8, which, for example, can be connected to a sewerage system via a pump.

Test Methods

Determination of the Compressibility Factor

The device for determination of the compressibility factor of a hygiene article comprises a Plexiglas cylinder which is closed at the bottom and has an internal diameter of 15 cm, a height of 40 cm and a wall thickness of 2 mm. At a height of 10 cm above the base of the cylinder is located a metal sieve having a mesh width of 400 μm and a wire diameter of 0.25 mm from ADMAR EUROPE, Sohren, Germany, art. no. 78185, which is connected permanently to the internal wall of the cylinder at a height of 10 cm above the base. The device for determination of the compressibility factor furthermore comprises a stamp of Plexiglas which can be inserted positively into the cylinder and can be weighted with metal weights. The total weight of the Plexiglas stamp and the metal weight is 10 kg.

For determination of the compressibility factor of a (unused) hygiene article, 0.9 wt. % strength NaCl solution (20 g per gram of superabsorbent material contained in the hygiene article) is introduced into the absorbent core of the hygiene article. After 60 minutes, the swollen hygiene article is introduced into the Plexiglas cylinder such that is comes to rest on the metal sieve, and is loaded with the stamp. The height of the stamp above the metal sieve is then determined ($H_1$).

The hygiene article is then removed from the cylinder and the trigger system is activated. Immediately after the trigger mechanism has been activated, the nappy is returned to the cylinder.

60 minutes after the trigger mechanism has been activated, the stamp is placed on the nappy again, the liquid released now running through the metal sieve into the base of the Plexiglas cylinder.

After a further 15 minutes, the height of the stamp above the metal sieve is determined again ($H_2$).

The compressibility factor K is defined as $K=(H_1/H_2)$

The invention claimed is:

1. A dehydratable hygiene article, comprising:
   a lower layer being impermeable to aqueous liquids;
   an upper layer being permeable to the aqueous liquids;
   a core disposed between said lower layer and said upper layer for absorbing the aqueous liquids;
   a trigger system having a superabsorbent material capable of absorbing aqueous liquids when transforming to a hydrogel, wherein after the trigger system has been activated, at least some of the aqueous liquid absorbed can be released from the superabsorbent material when it is present as said hydrogel; and
   at most 50 wt. % of a further superabsorbent material, based on a total weight of said superabsorbent material and said further superabsorbent material, which would be capable, after said trigger system has been activated, of at least partly absorbing, with the formation of said hydrogel, the aqueous liquid being at least partly released and only after a further trigger system differing from said trigger system has been activated, at least one of said trigger system and said further trigger system changing said superabsorbent material and said further superabsorbent material to have reduced absorbency capabilities to allow the aqueous liquid to be drained out from the dehydratable hygiene article thus allowing the dehydratable hygiene article to be further compressed for an extraction of more of the aqueous liquid resulting in the dehydratable hygiene article having a reduced volume.

2. A dehydratable hygiene article, comprising:
   a lower layer being impermeable to aqueous liquids;
   an upper layer being permeable to the aqueous liquids;
   a core disposed between said lower layer and said upper layer for absorbing the aqueous liquids; and
   a trigger system having a superabsorbent material capable of absorbing aqueous liquids with a transformation to a hydrogel, wherein after said trigger system has been activated, at least some of the aqueous liquid absorbed can be released from said superabsorbent material when it is present as said hydrogel, the dehydratable hygiene article containing the aqueous liquid having a compressibility factor, determined in accordance with a test method described herein, of at least 1.1 due to the aqueous liquid being removed out of the dehydratable hygiene article.

3. The dehydratable hygiene article according to claim 1, wherein:
   the dehydratable hygiene article is a nappy; and
   the reduced absorbency capabilities of the superabsorbent material and said further superabsorbent material are reduced by at least 60% based on a centrifuge retention capacity analysis.

4. The dehydratable hygiene article according to claim 1, wherein said trigger system has an acidic material disposed spatially separated from said superabsorbent material, and said superabsorbent material is an anionic superabsorbent material having absorption properties dependent on a pH, said trigger system is activated when it is made possible for said acidic material to come into contact with said hydrogel.

5. The dehydratable hygiene article according to claim 4, wherein said superabsorbent material is a crosslinked, partly neutralized polyacrylate and said acidic material is citric acid.

6. The dehydratable hygiene article according to claim 1, wherein:
   said superabsorbent material is a cationic superabsorbent material having absorption properties dependent on a pH; and
   said trigger system has a basic material disposed spatially separated from said superabsorbent material, and said trigger system is activated when it is made possible for said basic material to come into contact with said hydrogel.

7. The dehydratable hygiene article according to claim 1, wherein said trigger system has one of a neutral salt disposed spatially separated from said superabsorbent material and a neutral salt solution disposed spatially separated from said superabsorbent material, and said trigger system is activated when it is made possible for one of said neutral salt and said neutral salt solution to come into contact with said hydrogel.

8. The dehydratable hygiene article according to claim 1, wherein at least one of said lower layer and said upper layer has a closed outlet which can be opened and via which, after opening, the aqueous liquid at least partly released after said trigger system has been activated can be removed from the dehydratable hygiene article.

* * * * *